United States Patent [19]

Starks

[11] 4,093,667
[45] June 6, 1978

[54] PREPARATION OF 4-N-HEXYLRESORCINOL

[75] Inventor: Charles Masterson Starks, Ponca City, Okla.

[73] Assignee: Continental Oil Company, Ponca City, Okla.

[21] Appl. No.: 777,755

[22] Filed: Mar. 14, 1977

[51] Int. Cl.$^2$ ............................................. C07C 39/08
[52] U.S. Cl. ................................................... 568/766
[58] Field of Search ............... 260/625, 624 B, 613 B, 260/613 D, 621 F, 624 E, 624

[56] References Cited

U.S. PATENT DOCUMENTS

| | | | |
|---|---|---|---|
| 1,717,105 | 6/1929 | Hirzel et al. | 260/625 |
| 1,974,821 | 9/1934 | Kyrides | 260/625 |
| 2,030,423 | 2/1936 | Austin | 260/625 |
| 2,270,634 | 1/1942 | Isler | 260/625 |
| 2,874,141 | 2/1959 | Christenson | 260/625 |
| 2,999,098 | 9/1961 | Thompson | 260/625 |
| 3,256,336 | 6/1966 | Lange | 260/592 |
| 3,426,358 | 2/1969 | Schlichting et al. | 260/621 R |
| 3,639,490 | 2/1972 | Brown | 260/625 |
| 3,872,173 | 3/1975 | Berthoux | 260/624 C |
| 3,876,710 | 4/1975 | Saito | 260/624 C |

*Primary Examiner*—James O. Thomas, Jr.
*Assistant Examiner*—Werren B. Lone
*Attorney, Agent, or Firm*—Cortian R. Schupbach, Jr.

[57] ABSTRACT

Preparation of 4-n-hexylresorcinol is achieved by a two-step process involving: first preparing hexyl resorcyl ethers by reacting resorcinol with a hexylating agent having the general formula 1-$C_6H_{13}X$ in the presence of a base, and second, treating the reaction product obtained with a catalyst to yield 4-n-hexylresorcinol by a rearrangement process. X can be selected from the group consisting of Cl-, Br-, I-, $ArSO_3^-$, and similar materials.

9 Claims, No Drawings

PREPARATION OF 4-N-HEXYLRESORCINOL

This invention relates to a process for producing 4-n-hexylresorcinol in a two-step method. More specifically this invention relates to a method for the production of 4-n-hexylresorcinol by preparing hexyl resorcyl ethers by reacting resorcinol with a hexylating agent and rearrangeing the ethers thus obtained with a catalyst.

Many commercial applications exist for 4-n-hexylresorcinol which is an antiseptic and an anthelmintic. This particular compound is commercially prepared by condensing hexanoic acid with resorcinol and reducing the resulting ketone using a mercury-zinc amalgam. The prior art reaction is shown in equation 1.

Equation 1

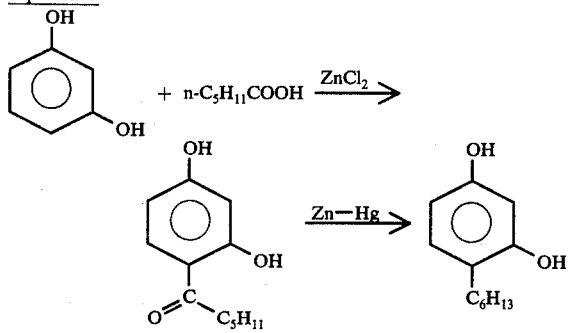

The condensation step encountered in the prior art process is not exceedingly difficult although a glass-lined reactor is normally required because of the zinc chloride involved. The zinc chloride can be regenerated and reused. The primary problem with the prior art procedure arises from the reduction using a zinc-mercury amalgam because of mercury contamination problems in a material consumed by humans. These contamination problems, combined with the exceedingly high cost of the zinc mercury amalgam, contribute to the high cost of 4-n-hexylresorcinol.

It would therefore be distinctly advantageous to provide a process for the production of 4-n-hexylresorcinol using a method which does not involve the expensive zinc-mercury amalgam with its attendant contamination problems, nor the condensation in the presence of toxic zinc chloride requiring glass-lined reactors and recovery of materials. It is desired that 4-n-hexylresorcinol be obtained rather than isohexylresorcinol, since isohexylresorcinol is not as desirable to act as an antiseptic and anthelmintic in humans.

An alternative route has been proposed whereby resorcinol can be directly alkylated, using materials such as methanol, over alumina catalysts. Such a reaction requires temperatures of 200° C to 400° C and produces water as a by-product. Removal of water is cumbersome and preferentially should be avoided. In addition, such a reaction is most efficient at pressures of about 300 psig, thus requiring equipment capable of withstanding such pressures.

It is therefore an object of the present invention to provide a method for the production of 4-n-hexylresorcinol. Other objects will become apparent to those skilled in this art as the description proceeds.

It has now been discovered in accordance with the instant invention that 4-n-hexylresorcinol can be prepared in a much more convenient method than those available to the prior art. The reaction is a two-step process. The first step involves the preparation of hexylresorcyl ethers by the reaction of resorcinol with a suitable hexylating agent in the presence of a base. The reaction product of this reaction is then heated in the presence of a suitable acidic catalyst to cause rearrangement of the ethers, preferably in the presence of some excess resorcinol, to ring-alkylated products, said products containing a predominance of 4-n-hexylresorcinol. The reactions are shown in equations 2 and 3 below. Equation 2 is the reaction occurring in the first step of the instant invention. For purposes of illustration the base utilized in the first step is assumed to be sodium hydroxide.

Equation 2

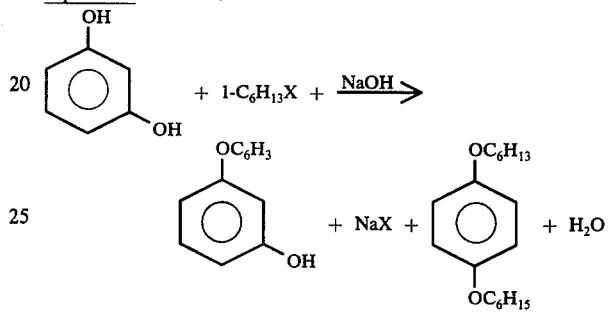

In the equation, X is selected from the group consisting of Cl—, Br—, I—, $CH_3SO_3$—, $ArSO_3$—, $C_2H_5SO_3$—, $C_2H_5OSO_3$—, $CH_3OSO_3$—, and $ONO_3$— or mixtures of these. The ethers shown as reaction products in equation 2 are the predominant products of the initial reaction, although some ring-alkylated compounds are also produced in the first stage.

The reaction mixture obtained as shown in equation 2 is then treated with a suitable acidic catalyst to cause rearrangement of the ethers shown. This reaction preferably, although not necessarily, takes place in the presence of some excess resorcinol to form ring-alkylated products, predominately 4-n-hexylresorcinol, as shown in equation 3.

Equation 3

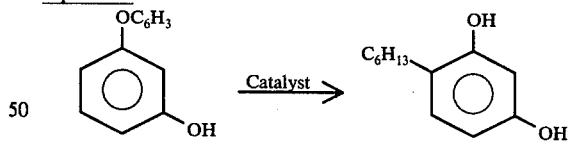

The reaction also produces other ring-alkylated compounds as by-products, all of which can be removed from main product by fractional distillation. Examples of such by-products are 2-n-hexylresorcinol, hexyl hexylresorcyl ethers, dihexyl resorcyl ether, dihexylether, and hexyl resorcyl ether. The main product for n-hexylresorcinol can be purified by any means well-known to those skilled in the art such as recrystallization or zone melting. Unreacted resorcinol and 1-hexanol can also be removed by fractional distillation and recycled for further use.

In carrying out the process of the instant invention, reaction temperatures of step 1 is usually from about 25° C to about 175° C and the reaction temperature of step 2 is from about 150° C to about 300° C. The catalyst of step 2 is an acidic catalyst such as alumina, silica alumina, methanesulfonic acid or a titania. The level of catalysts is generally not critical. However, the amount of catalyst controls the rate of the reaction. Since the product of 4-n-hexylresorcinol decomposes upon heating, the reaction conditions must be balanced so as to be as fast as possible while sufficient to reach an economical conversion level. This may require levels of catalysts of from about 1 weight percent to about 50 weight percent although from about 5 weight percent to about 20 weight percent are preferred.

The reaction is normally carried out at autogeneous pressure although higher pressures can be used.

The base used in part 1 of the instant invention is selected from the group consisting of the oxides, hydroxides, or carbonates of sodium, potassium, calcium, magnesium, ammonium, tetraalkyl ammonium and lithium. Representative examples of such bases are sodium hydroxide, tetraalkyl ammonium hydroxide, calcium hydroxide, calcium oxide, calcium carbonate and magnesia.

It is likewise preferred that the rearrangement of step 2 of the instant process be carried out in the presence of excess resorcinol. Normally, the excess resorcinol is present in a concentration of from about 5 to about 75 weight percent based on the total reaction mixture weight. The presence of this resorcinol increases the amount of 4-n-hexylresorcinol obtained from the process.

Additionally, it is preferred that the hexyl resorcyl ethers are prepared in the presence of an organic solvent such as toluene, hexanol, acetonitrile, N,N' dimethylformamide, dimethylsulfoxide, and methanol. While the presence of the solvent is preferred, this solvent is not essential to the process of the instant invention. Whether the solvent is used or not, the mole ratio of resorcinol to hexylating agent should range from about 1 to about 5 and preferably from about 2 to about 5 respectively, during the formation of the hexyl resorcyl ethers.

The di-n-hexylethers produced in step 1 of the instant invention, or from any source whatever, can likewise be reacted with resorcinol to form 4-n-hexylresorcinol in the presence of alumina catalysts. The reaction sequence in that shown in equation 4.

Equation 4

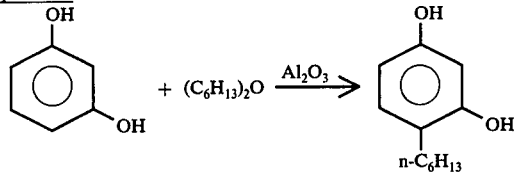

The reaction takes place under conditions similar to those set forth for the rearrangement depicted by equation 3. Temperatures of 150° C to 300° C can be used, but from 180° C to 250° C are preferred. Only alumina catalysts appear to be effective. Alumina catalysts derived from the water hydrolysis of aluminum alkyls are preferred for this reaction.

The invention is more concretely described with reference to the examples below wherein all parts and percentages are by weight unless otherwise specified. The examples are designed to illustrate the instant invention and not to limit it. Example 1 illustrates the first step of the instant invention. Example 2 illustrates the rearrangement of step 2 of the instant invention. Example 3 illustrates the process carried out in the absence of a solvent. Example 4 illustrates the reaction of di-n-hexylether to yield 4-n-hexylresorcinol.

EXAMPLE 1

Hexyl resorcyl ethers were prepared by stirring a mixture of 55 grams (.5 moles) of resorcinol, 82.5 grams (0.5 moles) of 1-bromohexane, 22 grams (0.55 moles) of sodium hydroxide, and about 50 ml of hexanol with heating temperature of 120° C the reaction became sufficiently exothermic to cause refluxing of the hexanol solvent. Additional hexanol was then added to control the reaction. After about two hours the reaction mixture was allowed to cool to room temperature and was washed with two 200 milliliter (ml) portions of water. The product organic phase was sampled and analyzed at this point and was discovered to contain the following composition;

|  | Area % |
| --- | --- |
| 1-hexanol | 47.97 |
| Resorcinol | 5.05 |
| Dihexylether | 1.06 |
| Hexyl resorcyl ether | 23.12 |
| Dihexyl resorcyl ether | 13.79 |
| 2-n-hexylresorcinol | 1.77 |
| 4-n-hexylresorcionl | 3.84 |
| Hexyl hexylresorcyl ethers | 2.98 |
| Other components | 0.42 | wherein the percentages are expressed as areas under a gas/liquid chromatograph curve.

This mixture was placed in a reaction flask together with 20 grams of powdered alumina and distilled so that essentially all of the hexanol and water were removed. The reaction mixture was then diluted with 175 ml of toluene filtered and washed with two 150 ml portions of water. Analysis of the organic product indicated that no reaction had occurred during distillation of the hexanol and dissolved water.

EXAMPLE 2

The reaction product of Example 1, in toluene solution, was added back to the reaction flask and toluene was distilled off until the reactor temperature reached 248° C. Toluene and water distillate were discarded. Fifty grams of resorcinol and 20 grams of alumina (powdered calcined CATAPAL alumina, trademark of and sold by Continental Oil Company) were added to the reaction mixture which was then heated to a temperature of 245° to 250° C for 3 hours. After cooling, the product was analyzed by gas chromatography and found to contain 17% 4-n-hexylresorcinol corresponding to a selectiveity of 28% for this product.

EXAMPLE 3

Sodium hydroxide (43g dissolved in 100 ml of water) was added slowly to a mixture of 110g. resorcinol, 165 g. 1-bromohexane, and 50 ml of water which was well stirred and heated under reflux. After addition was complete stirring and heating were continued for an additional 4 hours. After washing and acidification the aqueous layer was separated and the organic layer was further washed with two 500 ml portions of deionized water. The washed organic phase was then mixed with 100g. resorcinol and 40g. of calcined CATAPAL® alumina powder, and the resulting mixture heated with stirring to 220°-260° C for 3 hours. The resulting product contained a substantial proportion of 4-n-hexylresorcinol.

EXAMPLE 4

A mixture of 37.2 g. of di-n-hexyl ether and 55g of resorcinol, along with 10g. of calcined CATAPAL® alumina is heated, with stirring, to 180°–250° C for 5 hours. During this time the water that is produced is condensed in a Dean-Stark trap and separated from the reaction mixture. After cooling and removal of the catalyst, the reaction product can be analyzed gas chromatographically to find the amount of 4-n-hexylresorcinol.

While certain embodiments and details have been shown for the purpose of illustrating this invention, it will be apparent to those skilled in this art that various changes and modifications may be made herein without departing from the spirit or the scope of the invention.

I claim:

1. A process for the preparation of 4-n-hexylresorcinol comprising; a) preparing hexylresorcyl ethers by reacting recorcinol with a hexylating agent having the general formula 1-$C_6H_{13}X$ at a temperature of from about 25° C to about 175° C in the presence of a base selected from the group consisting of the oxides, hydroxides, or carbonates of sodium, potassium, calcium, ammonium, magnesium, tetra-alkyl ammonium, berium, and lithium, and b) heating the reaction product of (a) to a temperature of from about 150° C to about 300° C in the presence of an acidic catalyst to yield 4-n-hexylresorcinol, wherein X is selected from the group consisting of $Cl^-$, $Br^-$, $CH_3SO_3^-$, $C_2H_5SO_3^-$, $C_2H_5OSO_3^-$, $CH_3OSO_3^-$, $ArSO_3^-$, and $ONO_3^-$ or mixtures of these.

2. A process as described in claim 1 wherein (b) is carried out in the presence of excess resorcinol in a concentration of from about 5 to about 75 weight percent based on the total reaction mixture weight.

3. A process as described in claim 2 wherein (a) is carried out in the presence of an organic solvent.

4. A process as described in claim 3 wherein the organic solvent is selected from the group consisting of toluene, hexanol, aceto nitril, N,N'-dimethylformamide, dimethylsulfoxide, and methanol.

5. A process as described in claim 2 wherein the acidic catalyst of (b) is selected from the group consisting of alumina, silica alumina, titania, and methanesulfonic acid.

6. A process as described in claim 2 wherein the reaction temperature of (a) is from about 25° C to about 175° C and the reaction temperature of (b) is from about 150° C to about 300° C.

7. A process as described in claim 1 wherein the mole ratio of resorcinol to hexylating agent ranges from about 1 to about 5.

8. A process for the preparation of 4-n-hexylresorcinol comprising reacting di-n-hexylether with resorcinol in the presence of alumina catalysts at temperatures of from about 150° C to about 300° C.

9. A process as described in claim 8 wherein the mole ratio or di-n-hexylether to resorcinol is from about 1 to about 5.

* * * * *

UNITED STATES PATENT OFFICE
CERTIFICATE OF CORRECTION

PATENT NO. : 4,093,667
DATED : June 6, 1978
INVENTOR(S) : Charles M. Starks

It is certified that error appears in the above-identified patent and that said Letters Patent are hereby corrected as shown below:

First page, on line where Attorney, Agent, or Firm is listed - Cortian R. Schupbach, Jr. should be Cortlan R. Schupbach, Jr.

Column 6, line 1 please insert $I^-$ after $Br^-$.

Signed and Sealed this

Fourteenth Day of November 1978

[SEAL]

Attest:

RUTH C. MASON
Attesting Officer

DONALD W. BANNER
Commissioner of Patents and Trademarks